United States Patent [19]

Singh et al.

[11] Patent Number: 5,478,947
[45] Date of Patent: Dec. 26, 1995

[54] EFFECTIVE PROCESS FOR THE PRODUCTION OF 1,2,3-TRIAZOLES

[75] Inventors: Inder P. Singh; Paul Spevak; Bhupinder Palak; Samuel Amedjo, all of Edmonton; Ronald J. Micetich, Sher. Pk., all of Canada

[73] Assignee: SynPhar Laboratories, Inc., Edmonton, Canada

[21] Appl. No.: 282,027

[22] Filed: Jul. 29, 1994

[51] Int. Cl.$^6$ .................................................. C07D 249/04
[52] U.S. Cl. .................................................... 548/255
[58] Field of Search ........................................ 548/255

[56] References Cited

U.S. PATENT DOCUMENTS 4,950,673  8/1990  Bochis et al. ............................ 514/314

FOREIGN PATENT DOCUMENTS 1-143861  6/1989  Japan ...................................... 548/255

*Primary Examiner*—Patricia L. Morris
*Attorney, Agent, or Firm*—Nikaido, Marmelstein, Murray & Oram

[57] ABSTRACT

A high purity triazole is obtained by the reaction of a hydrazide of the general formula II and glyoxal followed by the treatment of the intermediate of general formula IV with ammonia. The total process is done in one pot and does not require the isolation of the intermediate IV. The triazole (I) is isolated by distillation. Synthesis of various $N_1$-substituted triazoles is also described following the same procedure.

13 Claims, No Drawings

EFFECTIVE PROCESS FOR THE PRODUCTION OF 1,2,3-TRIAZOLES

BACKGROUND OF THE INVENTION

1. Field of the Invention

The present invention is concerned with the production of 1,2,3-triazoles by a simple, safe and economically viable method utilizing cheap and non-toxic chemicals. The unsubstituted 1,2,3-triazole is required as an intermediate in the synthesis of useful pharmaceutical products such as Tazobactam (EP 331395 A1 890906) and substituted 1,2,3-triazoles are required as intermediates in the preparation of various other pharmaceuticals or pesticides (JP 05222006 A2 930831 Heisei, JP 05148280 A2 930615 Heisei, JP 05112536 A2 930507 Heisei and EP 433842 A2 910626).

2. Description of Related Art

A current method for the preparation of 1,2,3-triazole is by the reaction of azido derivatives with acetylene under pressure, followed by reductive cleavage of the protecting group (Japan Kokai Tokyo Koho JP 1-143861), as summarized below:

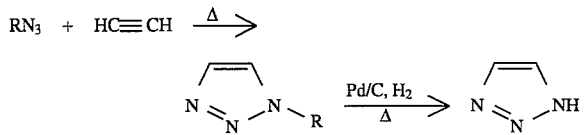

One of the serious drawbacks of this method is the explosive nature of azides, acetylene and of the catalyst Pd/C (Japan Kokai Tokyo Koho JP 5-140121). The reaction also requires high pressure conditions. Due to the explosive nature of the reactants and the cost of catalyst, this process is hazardous and uneconomical.

Another method utilizes a two stage process and requires chemicals (i.e. dichloroacetaldehyde) that are toxic and difficult to handle, particularly on a large scale. Dichloroacetaldehyde is toxic and tends to polymerize on standing, as well as in contact with acids, such as propionic acid that is used as the solvent in the first step of the process. The reactions are summarized below.

Step I

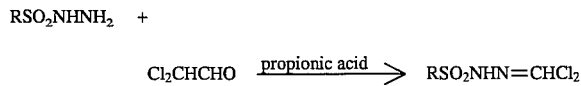

Step II

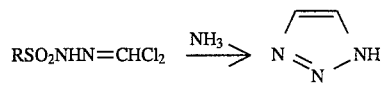

In Step I, propionic acid is used as the solvent. The main drawbacks of this process are the relative unavailability of dichloroacetaldehyde and its toxicity, as well as its tendency to polymerize under the reaction conditions employed. The product obtained at the end of the first step needs to be purified to remove completely any remaining propionic acid. The presence of propionic acid leads to byproducts in the triazole which are difficult to remove at the end of the second step. The isolation and purification of the hydrazone intermediate is a problem in this process.

The described procedure also does not provide an economical isolation method for the triazole from the reaction mixture. The method described indicates isolation using column chromatography and this is not economically viable for large scale production.

SUMMARY OF THE INVENTION

The present patent provides a one-pot, safer, economical method, that utilizes commercially available, non-toxic, cheap alternatives to dichloroacetaldehyde. The total process is done using one solvent in a one-pot reaction and without the need for isolation of the intermediate III from the reaction mixture. The reactions are summarized as follows:

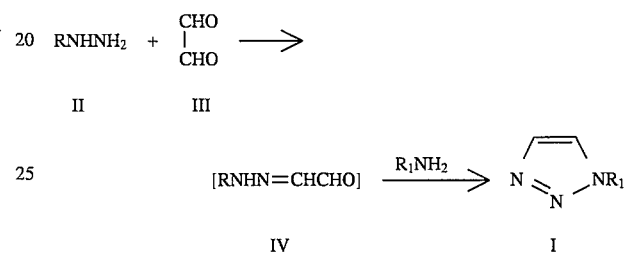

The hydrazide plus glyoxal produces the hydrazone intermediate which is treated with ammonia or amine to give the trizole.

DESCRIPTION OF THE PREFERRED EMBODIMENTS

In a typical example, the reaction of a compound of the general formula II with glyoxal gives the intermediate hydrazone (IV) prepared in situ which on reaction with ammonia produces the triazole or on reaction with appropriately substituted amines produces corresponding $N_1$-substitute triazoles. The 1,2,3-triazole is recovered from the reaction mixture by distillation under reduced pressure. In the case of substituted triazoles, distillation or column chromatography can be used to isolate the product. The whole process is done with or without an acid or base catalyst.

The hydrazides used in this patent are of the general formula II where R represents R'CO and R'SO$_2$; in which R' can be a lower alkyl such as methyl, ethyl, propyl, cyclopropyl, isopropyl, butyl, isobutyl which may be further substituted with halogens such as chloro, bromo or fluoro, or a phenyl group that can be further substituted with chloro, fluoro, bromo, nitro, lower alkyl or lower alkoxy.

The dialdehyde glyoxal can be in the free form or as a solution of glyoxal in water or as the polymer or protected as a stable acetal derivative.

The amines used in the present process are of general formula $R_1NH_2$, where $R_1$ represents H, alkyl or aryl groups. An alkyl group can be a methyl, ethyl, propyl, cyclopropyl, isopropyl, butyl, isobutyl which may be further substituted with a phenyl group that can be further substituted with chloro, fluoro, bromo, or nitro, lower alkyl or lower alkoxy. $R_1$ can also be phenyl or a substituted phenyl that can be further substituted with chloro, fluoro, bromo, nitro, lower alkyl or lower alkoxy. $R_1$ may also be a heterocyclic group.

The ammonia used in this reaction can be in the gaseous form and bubbled directly into the reaction mixture or liquid ammonia or a solution of ammonia in water or in a suitable organic solvent.

The solvents used in the procedure of this patent can be water or any of the following or a mixture thereof: lower alkylalcohols, such as methanol ethanol, propanol, isopropanol, butanol; alkyl ethers such as diethyl, ethyl methyl, isopropyl ether, halogenated hydrocarbons such as dichloromethane, chloroform, carbon tetrachloride and other solvents such as DMSO, DMF, $CH_3CN$, dioxane or diphenyl ether.

The ratio of glyoxal to hydrazide may vary from 2 to 10 moles of glyoxal to every one mole of hydrazide, however 2 to 4 moles of glyoxal for every mole of hydrazide is preferred. The reaction temperature may vary from $-30°$ to $70°$ C., but the preferred temperature is between $20°$ and $55°$ C. The time for the reaction varies with reactants and the solvent as well as if a catalyst is used, however a reaction time of 1–18 hours is preferred.

The method of reacting the hydrazide derivatives with glyoxal can be varied. For example, both may be dissolved simultaneously into a solvent and after the initial reaction is over, ammonia is bubbled through. Alternatively, a solution of hydrazide is added to a solution of glyoxal or vice versa and then $NH_3$ is added as a gas or in a solution form or ammonia and the hydrazide are added together to a cooled, stirred solution of glyoxal. The reaction mixture is cooled to $-30°$ C. if liquid ammonia is to be used. For the process to produce substituted triazoles, the substituted amine may be added to the mixture at once or in aliquots.

The reaction can be done in the presence of an organic carboxylic acid or a mineral acid; in the presence of a basic catalyst such as ammonia or a metal hydroxide or without using any catalyst.

The triazole is isolated from the reaction mixture in the following way. The ammonia and the solvent if low boiling is removed by distillation and the residue extracted with a mixture of methanol and ether or with chloroform or methylene chloride. The extract is then concentrated. The triazole is obtained in 25 to 48% yields by fractional distillation of the oily residue.

The acids used in this patent can be an aliphatic carboxylic acid such as formic, acetic, propionic, isopropionic, butyric or isobutyric acid; an aromatic carboxylic acid or an aliphatic or aromatic sulfonic acid or a mixture there of, inorganic mineral acids such as hydrochloric, sulfuric acid, etc.

EXAMPLE 1

A solution of p-toluene sulfonyl hydrazide (5 gm) and gl. acetic acid (0.25 ml) in methanol (45 ml) was added drop-wise into a stirred solution of glyoxal (7.75 ml of 40% solution) in methanol (25 ml). Some solid separated out during the addition. The reaction mixture was then stirred for additional 15 minutes. A stream of ammonia was bubbled through maintaining the temperature under $40°$ C. for 30 minutes. The reaction mixture was left stirring at room temperature overnight. The reaction mixture was concentrated and diluted with 25% methanol in ether (250 ml). The separated solid was removed by filtration, the filtrate concentrated and the residue distilled to isolate triazole (0.8 gm, 44.5%). The fraction collected at $42°$ C. (.25 mm) was identified at 1,2,3-triazole. NMR ($CDCl_3$) δ: 7.76 ppm (2H).

EXAMPLE 2

To a stirred solution of glyoxal (7.75 ml of 40% solution) and gl. acetic acid (0.25 ml) in methanol (45 ml) was added portion-wise solid p-toluene sulfonyl hydrazide (5 gm). The clear reaction mixture was then stirred for 60 minutes. A stream of ammonia was bubbled through the reaction mixture for 45 minutes. During the ammonia addition the reaction temperature rose to $55°$ C. and then slowly dropped to $30°$ C. The reaction mixture was left stirring at room temperature overnight. The reaction mixture was concentrated, and diluted with 25% methanol in ether (250 ml). The separated solid was removed by filtration, the filtrate concentrated and the residue distilled to isolate triazole (0.98 gm, 53%). The fraction collected at $42°$ C. (0.25 mm) was identified at 1,2,3-triazole (769 mg, 53.4%). NMR ($CDCl_3$) δ: 7.76 ppm (2H).

EXAMPLE 3

A solution of p-chlorobenzene sulfonyl hydrazide (4 gm) and gl. acetic acid (0.30 ml) in 40 ml of methanol was added dropwise into a stirred solution of glyoxal (5.6 ml of 40% solution in water) in 20 ml of methanol at room temperature. The reaction mixture was stirred for an additional 25 minutes. To the resultant suspension ammonia was bubbled slowly to maintain the temperature between $20°$ to $30°$ C. The flow of $NH_3$ was stopped after 30 minutes. The resultant clear reaction mixture was then left stirring at room temperature for 18 hours. The solvent was removed under reduced pressure and the residue extracted with ether. The ether extract was concentrated and the oily residue was subjected to fractional distillation. The 1,2,3-triazole was isolated as a fraction boiling at $42°$ C. (0.25 mm). NMR ($CDCl_3$) δ: 7.76 ppm (2H).

EXAMPLE 4

40 ml of methanol was placed in a three neck flask equipped with a thermometer, reflux condenser and a gas inlet for the introduction of ammonia. p-toluene sulfonyl hydrazide (5 gm) and glyoxal solution (7.75 ml of 40% solution) were added together under stirring. Within five minutes the flow of ammonia gas was started. Gradually, all reactants went into solution. The temperature rose to $55°$ C. and then slowly dropped to $40°$ C. The flow of ammonia stopped and the reaction mixture stirred for an additional 18 hours. The separated solid was filtered off and the filtrate was concentrated to an oily residue. Triazole was recovered by fractional distillation of the residue (1.172, 63.35%). NMR ($CDCl_3$) δ: 7.76 ppm (2H).

EXAMPLE 5

A solution of glyoxal (7.75 ml of 40% solution) in methanol (25 ml) was added drop-wise into a solution of m-nitro-benzoic acid hydrazide (5 gm) in methanol (90 ml) at $40°$ C. Some solid separated out during the addition. The reaction mixture was then stirred for an additional 15 minutes. A stream of ammonia was bubbled through the reaction mixture maintaining the temperature under $40°$ C. for 30 minutes. The reaction mixture was left stirring at room temperature overnight. The separated solid was removed by filtration and washed with a solution of 25% methanol in ether (250 ml), the filtrate was concentrated and the 1,2,3-triazole was isolated by fractional distillation of the resultant oily residue (448 mg, 24.2%). NMR ($CDCl_3$) δ: 7.75 ppm (2H).

EXAMPLE 6

To a solution of glyoxal (7.75 ml of 40% solution) and acetic acid (0.25 ml) in 75 ml of methanol, was added solid p-toluene sulfonyl hydrazide (5 gm, 0.0268 m) under stirring. The reaction mixture was stirred for an additional 60 minutes. To this resultant suspension benzyl amine (3.09 gm) was added at once and then left stirring at room temperature for 18 hours. The solvent was removed and the residue extracted with ether. The ether extract was concentrated and $N_1$-benzyl-1,2,3-triazole (2.01 gm, 50.25%) was recovered from the oily residue by distillation under high vacuum. NMR (CDCl$_3$) δ: 5.52 (s, 2H), 7.34 (m, 4H), 7.55 (s, 1H), 7.72 (s, 1H) ppm.

EXAMPLE 7

To a solution of glyoxal (3.5 ml of 40% solution) and acetic acid (0.12 ml) in 40 ml of methanol, was added solid p-toluene sulfonyl hydrazide (2.5 gm, 0.0134 m) under stirring. The reaction mixture was stirred for an additional 60 minutes. To this resultant suspension ethyl amine (1.809 gm, 0.0402 m) was added at once and then left stirring at room temperature for 18 hours. The solvent was removed and the residue extracted with ether. The ether extract was concentrated and the $N_1$-ethyl-1,2,3-triazole recovered from the oily residue by chromatography over silica gel column (yield 582 mg, 56.5%). NMR (CDCl$_3$) δ: 1.56 (t, 3H), 4.47 (q, 2H), 7.60 (s, 1H), 7.7 (s, 1H) ppm.

EXAMPLE 8

To a solution of glyoxal (3.5 ml of 40% solution) and acetic acid (0.12 ml) in 40 ml of methanol, was added solid p-toluene sulfonyl hydrazide (2.5 gm, 0.0134 m) under stirring. The reaction mixture was stirred for an additional 60 minutes and then cooled to 5° C. Cyclopropyl amine (0.76 gm, 0.0134 m) was added dropwise while maintaining the temperature of the reaction under 10° C. The temperature of the reaction mixture was raised slowly to room temperature over 30 minutes, and stirring continued for an additional 20 hours. The solvent was removed and the residue extracted with ether. The ether extract was concentrated and the $N_1$-cyclopropyl-1,2,3-triazole was recovered from the oily residue by chromatography over silica gel column (yield 641 mg, 43.75%). NMR (CDCl$_3$) δ: 1.26 (m, 4H), 3.78 (m, 1H), 7.6 (s, 1H), 7.66 (s, 1H) ppm.

We claim:

1. A method of producing 1,2,3-triazole, $N_1$-alkyl 1,2,3-triazole or aryl 1,2,3-triazole comprising reacting hydrazides of the formula II

RNHNH$_2$          (II), with glyoxal, and ammonia or an appropriately substituted amine, wherein R is R'CO or R'SO$_2$ in which R' is a lower alkyl which is unsubstituted or substituted with halogens, or R' is a phenyl group which can be further substituted with chloro, fluoro, bromo, nitro, lower alkyl or lower alkoxy.

2. The method of claim 1 wherein R' is selected from the group consisting of methyl, ethyl, propyl, cyclopropyl, isopropyl, butyl, or isobutyl, which may be unsubstituted or substituted with chloro, bromo, or fluoro.

3. A method of producing 1,2,3-triazole comprising
   a) adding a solution of p-toluene sulfonyl hydrazide to a solution of glyoxal in the presence of acetic acid, and
   b) subsequently adding of NH$_3$ gas.

4. The method of claim 3 wherein the method is carried out in one pot.

5. A method of producing 1,2,3-triazole comprising adding NH$_3$ gas to a mixture of p-toluene sulfonyl hydrazide and glyoxal in the presence of acetic acid.

6. The method of claim 5 wherein the method is carried out in one pot.

7. A method for the production of 1,2,3-triazole comprising
   a) adding a glyoxal solution to a solution of p-chlorobenzene sulfonyl hydrazide in the presence of acetic acid, and
   b) subsequently adding NH$_3$ gas.

8. The method of claim 7 wherein the method is carried out in one pot.

9. A method for the production of 1,2,3-triazole comprising
   a) adding glyoxal solution into a solution of m-nitro benzoyl hydrazide in the presence of acetic acid, and
   b) subsequently adding NH$_3$ gas.

10. The method of claim 9 wherein the method is carried out in one pot.

11. A method for the production of 1,2,3-triazole comprising
    a) adding solid p-toluene sulfonyl hydrazide into a stirred solution of glyoxal and acetic acid in methanol, and
    b) subsequently adding ammonia gas.

12. The method of claim 11 wherein the method is carried out in one pot.

13. A method of producing $N_1$-benzyl-1,2,3-triazole, $N_1$-ethyl-1,2,3-triazole, or $N_1$-cyclopropyl-1,2,3-triazole comprising reacting glyoxal, p-toluene sulfonyl hydrazide, and an appropriately substituted amine to give corresponding $N_1$-substituted-1,2,3-triazole.

* * * * *